United States Patent [19]
Brigham

[11] Patent Number: 5,411,136
[45] Date of Patent: * May 2, 1995

[54] ORTHODONTIC BAND STERILIZATION CASSETTE

[76] Inventor: Susan K. Brigham, 7324 E. Ironwood Ct., Scottsdale, Ariz. 85258

[*] Notice: The portion of the term of this patent subsequent to Apr. 26, 2011 has been disclaimed.

[21] Appl. No.: 230,601

[22] Filed: Apr. 21, 1994

Related U.S. Application Data

[60] Division of Ser. No. 121,698, Sep. 15, 1993, Pat. No. 5,305,876, which is a continuation-in-part of Ser. No. 33,290, Mar. 16, 1993, abandoned, which is a continuation of Ser. No. 811,657, Dec. 23, 1991, abandoned.

[51] Int. Cl.⁶ .......................... A61L 2/00; B65D 81/00
[52] U.S. Cl. .................... 206/63.5; 206/459.5; 422/297; 422/300
[58] Field of Search ............... 206/63.5, 363–370, 206/438, 439, 459.5; 220/345; 422/297, 300, 310; 433/23, 77, 97

[56] References Cited

U.S. PATENT DOCUMENTS

| | | | |
|---|---|---|---|
| 2,701,635 | 2/1955 | Mills . | |
| 2,739,734 | 3/1956 | Pugh . | |
| 3,092,443 | 6/1963 | Dietz | 206/350 |
| 4,015,333 | 4/1977 | Dellinger et al. | 433/23 |
| 4,333,567 | 6/1982 | Leonard | 206/368 |
| 4,402,407 | 9/1983 | Maly | 206/438 |
| 4,854,475 | 8/1989 | Rilhimaki | 220/337 |
| 4,898,276 | 2/1990 | Georgakis | 206/369 |
| 4,959,199 | 9/1990 | Brewer | 422/300 |
| 4,978,510 | 12/1990 | Smith | 422/310 |
| 5,022,858 | 6/1991 | Castellini | 433/97 |
| 5,084,251 | 1/1992 | Thomas | 422/300 |
| 5,131,532 | 7/1992 | Ives | 422/300 |

FOREIGN PATENT DOCUMENTS 0306311 2/1929 United Kingdom ................ 220/345

Primary Examiner—Jimmy G. Foster
Attorney, Agent, or Firm—Donald J. Lisa

[57] ABSTRACT

A multiple compartment box for use in sterilizing and segregating small parts, such as orthodontic bands. The box is shaped as a cassette and is divided into a plurality of small compartments by a plurality of dividers, which include at least one intersecting divider mutually perpendicular to the other dividers. The entire cassette including dividers and lid is preferably made of a material which is resistant to repeated sterilization processing, such as, a metal. Each compartment is identified with respect to an orthodontic band associated with a particular jaw, quadrant and tooth of a patient's mouth to assist is segregating and differentiating the band. The dividers have substantially flat edges which closely abut the inner adjoining surfaces of the sidewalls, endwalls, base and lid to prevent passage of bands identified for one compartment to another compartment. The box incorporates a sliding lid which can be opened or closed without interfering with the divider edges or the contents of the compartments.

14 Claims, 1 Drawing Sheet

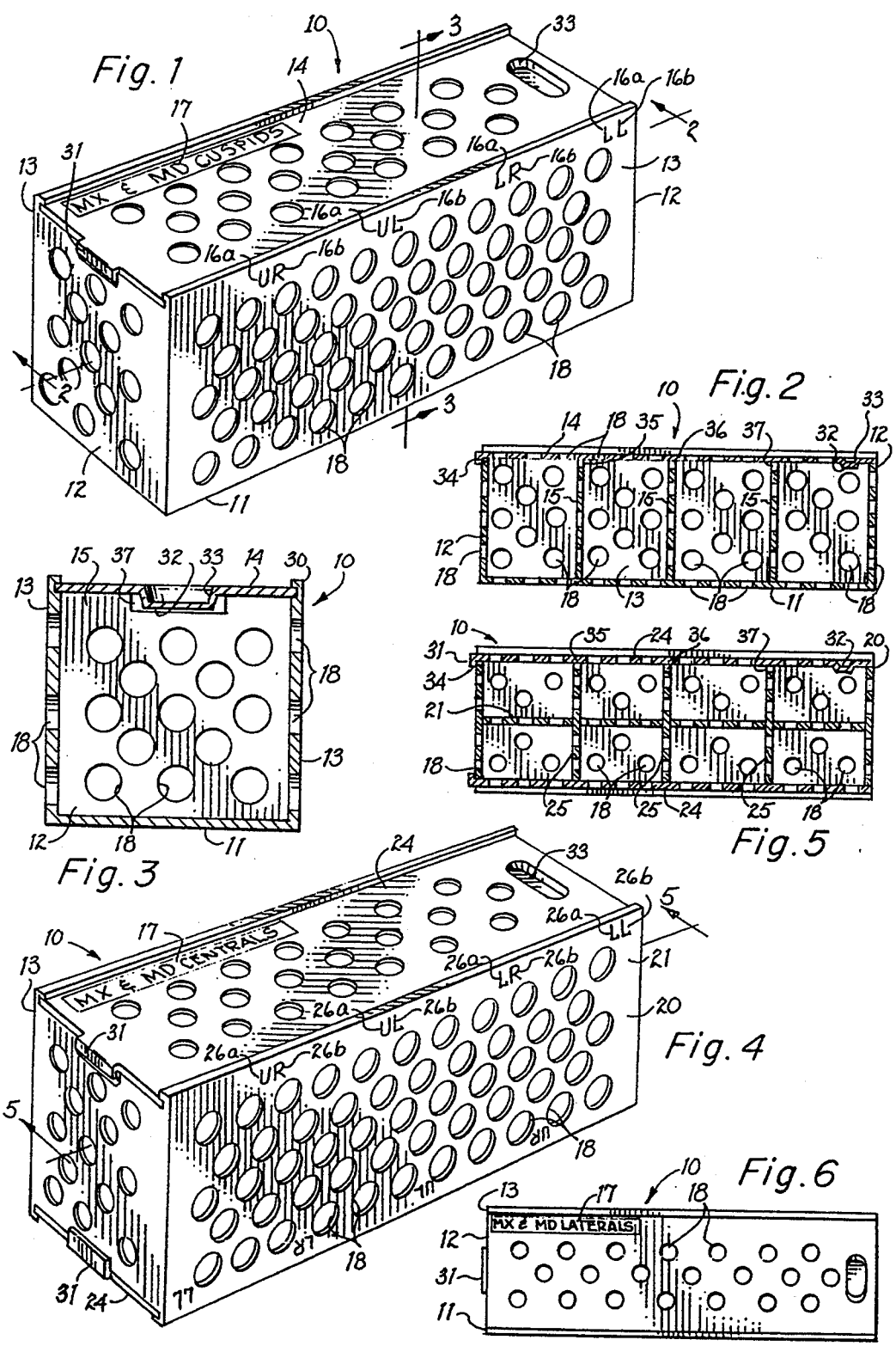

1

ORTHODONTIC BAND STERILIZATION CASSETTE

RELATED APPLICATION

This application is a divisional of patent application Ser. No. 08/121,698 filed Sep. 15, 1993, U.S. Pat. No. 5,305,876, which is a continuation-in-part application of Ser. No. 08/033,290 filed Mar. 16, 1993, now abandoned, which is a continuation application of Ser. No. 07/811,657 filled Dec. 23, 1991, now abandoned.

BACKGROUND OF INVENTION

The invention relates to the field of sterilization devices. It further relates to cassettes used to hold small parts to prevent their loss or damage during the sterilization process.

It is a common problem in the fitting of orthodontic bands that many of the bands are lost or damaged during the fitting, cleaning or sterilizing process. A further problem is the large number of orthodontic bands. There are 32 different sized bands for each of 28 teeth, making a total of 896 different sized bands. In fitting orthodontic bands it is frequently necessary to try numerous variously sized orthodontic bands until the appropriately sized band is found for a particular tooth. Each band which is attempted and not appropriately sized is removed from the mouth and then placed on a counter until the fitting process is completed. After the fitting is completed it is necessary for the orthodontist or an assistant to collect the unused bands, wash them by hand and then collect the bands and sterilize them. Due to the small size of the bands, they are easily dropped or mishandled which can cause them to be lost or damaged. Further, after the bands are removed from sterilization, they must be sorted by hand, and replaced in the appropriate containers for the next use. This sorting requires a great deal of time and effort.

The placement of the orthodontic bands on a counter after they have been removed from a patients mouth increases the possibility that the orthodontist or his or her assistants may come into contact with the bands which are exposed to oral fluids. This increases the risk to the orthodontist or assistants of exposure to germs or disease.

Many type of cassettes or boxes are known for use in sterilizing equipment used in a medical or dental setting. Examples of these inventions are shown in the Brewer patent, U.S. Pat. No. 4,959,199 which discloses a cassette used for the sterilization of dental instruments; the Riihimaki et al patent, U.S. Pat. No. 4,854,475 which discloses a cassette for sterilizing dental instruments; the Maly patent U.S. Pat. No. 4,402,407 which discloses a surgeon's chest for sterilizing surgical instruments; and the Dietz patent U.S. Pat. No. 3,092,443 which discloses a dental burr holder and sterilizer.

The art also discloses boxes for storage of small parts such as orthodontic brackets as shown by the Georgakis patent, U.S. Pat. No. 4,898,276.

The problem in the art is that most of the sterilization devices are designed for the sterilization of dental instruments which are of a sufficient size that there is little risk of these items being lost in the sterilization process. Further dental and surgical instruments are of sufficient size and strength so that they are not likely to be damaged during the handling or processing necessary in the sterilization phase. There is not known a cassette manufactured of sufficient materials to readily withstand repeated use in the dental sterilization process and which can be used to hold small parts, such as orthodontic bands and that can assist in the segregation and organization of these parts.

Another problem with the current method of sterilizing orthodontic bands is that they are often placed in standard autoclave bags for sterilization. These bags are disposed of after each use which causes a repeated expense.

SUMMARY OF THE INVENTION

The present invention is a sterilization cassette which includes two generally parallel sidewalls and two generally parallel endwalls generally perpendicular to the sidewalls, the sidewalls and endwalls being attached to a base also generally perpendicular to the sidewalls, the sidewalls, endwalls and base defining a generally rectangular container having an upper opening adjacent an upper edge of the sidewalls and endwalls. The cassette has a plurality of a first set of dividing wall members supported in the container, each having end, top and bottom edges, which thereby define a plurality of discrete compartments within the rectangular container. Also included is a generally flat lid portion operably associated with the upper edge of the side or end walls to releaseably close the upper opening. Each of the compartments is labelled with a first indicia identifying a jaw of a patient's mouth and a second indicia identifying a quadrant of a patient's mouth. A third indicia is disposed on the container or lid identifying each of the discrete compartments with respect to an associated orthodontic band for a tooth. The cassette has a plurality of openings in the container or lid for admitting a sterilization liquid to each compartment for sterilizing orthodontic bands placed therein. Each of the divider edges are closely abutting its associated adjacent inner surface of the base, wall and lid, respectively, and are sufficiently flat to prevent passage therebetween of an orthodontic band identified for one compartment to an adjacent compartment.

A further feature of the invention is a slidable lid which includes an inner groove at an upper edge of each sidewall with a generally flat lid portion engaging and reciprocable within the grooves to open and close the container without interference with the top edges of the dividing wall members or the contents of the compartments.

A still further feature of the invention is that the entire cassette and all dividing wall members may be made of metal, such as, stainless steel, that can withstand repeated sterilization processing.

Another feature of the invention is that the first set of dividing wall members are generally parallel to the endwalls of the cassette and are each generally perpendicularly intersected by, or interlocking with, at least one of a second set of dividing wall members which is generally parallel to the sidewalls thereby further dividing the cassette into discrete compartments.

It is an object of the invention to provide a cassette which prevents or minimizes the loss or damage to orthodontic bands occurring during the fitting and sterilization process.

It is a further object of the invention to provide a cassette which allows for the segregation of orthodontic bands during the fitting process by dividing the cassette into a plurality of easily accessible discrete compartments each of which is identified to particular bands which are prevented from passing to other compartments during the sterilization process.

It is a further object of the invention to provide a sterilization cassette which reduces the time spent sorting orthodontic band or other small parts after sterilization.

It is a further object of the invention to provide a cassette which assists in maintaining a clean and sterile environment in an orthodontic or dental office during the procedure of fitting orthodontic bands.

It is a further object of the invention to provide a reusable sterilization cassette which reduces the cost of sterilizing orthodontic bands.

BRIEF DESCRIPTION OF THE DRAWINGS

FIG. 1 is a perspective view of one embodiment of the present invention.

FIG. 2 is a cross-section view of the present invention taken along line 2—2 of FIG. 1.

FIG. 3 is an cross-section view of the present invention taken along line 3—3 of FIG. 1.

FIG. 4 is a perspective view of a second embodiment of the present invention.

FIG. 5 is a cross-section view of the second embodiment of the present invention taken along line 5—5 of FIG. 4.

FIG. 6 is a top view showing the lid of the second embodiment of the present invention.

DETAILED DESCRIPTION OF THE PREFERRED EMBODIMENT

The present invention consists of a cassette with multiple compartments for temporary storage of orthodontic bands during the sterilization process. As shown in FIG. 1, the cassette 10 is formed in the shape of a box having base 11, endwalls 12, and two substantially parallel sidewalls 13. Dividers 15 are shown in FIG. 2, which is a cross-section view of the cassette. The dividers 15 which separate the container into multiple compartments may be either movable or immovable and they extend generally from the base of the cassette to a point near groove 30, shown in FIG. 3, which is near the top of sidewalls 13. Each of the dividers 15 have edges closely abutting its associated adjacent inner surface of the base, wall and lid, respectively, the edges being sufficiently flat to prevent passage therebetween of an orthodontic band identified for one compartment to an adjacent compartment.

The cassette 10 comprises a lid 14 which slides open to allow access to the interior compartments of the cassette 10. The cassette 10 further comprises a first indicia 16a which identifies each compartment of the cassette 10 with respect to the jaw of the patient's mouth, such as upper (maxillary) or lower (mandibular) and a second indicia 16b which, when taken with the first indicia 16a, identifies each quadrant of a patient's mouth (upper right, upper left, lower right, lower left). A third indicia 17, such as a label, indicates the contents of the cassette. Third indicia 17 is used to identify each cassette if multiple cassettes are used. It is anticipated that multiple cassettes will be used by an orthodontist in the band fitting process.

When used for segregation of orthodontic bands third indicia 17 will indicate the type of tooth the bands are designed for, such as maxillary and mandibular cuspids, maxillary and mandibular 1st bicuspids, maxillary and mandibular 2nd bicuspids, maxillary and mandibular 1st molars, maxillary and mandibular 2nd molars, maxillary and mandibular centrals, and maxillary and mandibular laterals, and the first and second indicia 16a and 16b will further segregate the bands by indicating whether they are for an upper or lower (jaw) right or left (quadrant) tooth. Taken together, the three indicia identify a particular tooth in the patient's mouth with each compartment. Other indicia could of course be used for a different segregation method.

The lid 14 for the cassette 10 consists of a sliding member which slides in a groove 30 which is incorporated into the top of the sidewalls 13, as shown in FIG. 3. This sliding lid 14 could include a lip, such as shown by 31, which acts as a stop when closing the lid by abutting against end wall 12. During normal operation, the left (as seen in FIG. 1) edge of protuberance 32 of finger slot 33 is designed to prevent full removal of the sliding member by abutting against the inside surface of end wall 12 beneath half slot 34 formed therein (FIG. 2) while passing easily through full slots 35, 36, 37 (FIG. 3) formed in the top of dividing wall members 15. The half and full slots are sized to prevent identified bands for one compartment from passing through the slots to another compartment. Lid 14 may be initially inserted over the bottom edge of half slot 34 during installation by the exertion of a slight pressure which will cause a small upward flex in lid 14 allowing protuberance 32 to pop over the top of wall 12 through half slot 34, and thereafter act as an effective stop preventing inadvertent removal of lid 14. The lid 14 is selectively held open or closed by friction with the groove 30 in which it slides. The lid 14 slides in the direction indicated by arrow 3 in FIG. 1 in order to close cassette 10. Lid 14 allows selective access to the interior compartments.

Further if it is desired, the lid 14 could be securely closed with a variety of known methods. One such method would be to incorporate notches (not shown) at predetermined places in the groove 30 in which the lid 14 slides and a spring activated lever (not shown) which engages said notch. The lever could be released by the orthodontist or assistant manually releasing the lever. Other simple type of mechanisms to allow the lid to be releasably secured in an open, partially open or closed position are commonly known.

The cassette 10 is manufactured with a perforated material used for the sidewalls, endwalls, and dividers. The lid and the base may be made out of solid or perforated materials. It is preferable to manufacture the base from a solid material so that bodily fluids or other contaminants on the bands do not pass from the cassette onto a working surface. The perforations are shown as numeral 18. The perforations 18 allow steam to penetrate the cassette 10 if it is used in an autoclave. The perforations also allow for sterilizing liquids to penetrate the cassette 10 to sterilize the small parts, such as the orthodontic bands, placed in the cassette. The perforations are sized so that the small parts, such as, orthodontic bands, placed in cassette 10 cannot pass through the perforations. The perforations are sized to prevent the movement of parts between the multiple compartments of cassette 10.

The cassette 10 can be manufactured from any material that can be repeatedly sterilized and can withstand the stress of being repeatedly used in an autoclave or repeatedly exposed to sterilizing liquids. An acceptable material would be surgical steel.

The cassette is used by the orthodontist during the process of fitting orthodontic bands. Usually during this process the orthodontist works on locating a properly sized band for a specific tooth by trial and error, selecting a certain sized band and attempting to fit it on the tooth. If the band is appropriately sized it is fitted to the tooth. If the band is the wrong size, the band which was attempted is placed in the appropriately labelled compartment of the appropriately labelled cassette. The cassette indicating the appropriate indicia for the specific tooth being worked on by the orthodontist would be placed in close proximity to the orthodontist. The cassette 10 would be placed on a counter or other flat surface near the orthodontist. The flat base 11 would be placed on the flat surface. In this orientation the lid 14 would be on the top of the cassette. The lid 14 slides open to allow the attempted bands to be placed in the corresponding marked compartment in the cassette. In this way the bands are segregated to allow for ease of sorting after sterilization. It is common after sterilization to return the bands to the original manufacturers containers.

A second embodiment of the invention is shown in FIGS. 4 and 5. In this embodiment, the cassette 20 is constructed in a manner similar to the cassette 10, except that this cassette does not have a sealed base member. Rather this cassette 20 incorporates two slidable lids 24 on opposite side of the cassette 20. In addition to the vertical dividers 25, the cassette 20 also comprises a horizontal divider 21 which perpendicularly intersects with each of the vertical dividers 25 and also separates the cassette into a lower and an upper portion. Preferably, dividers 21 and 25 are perpendicularly intersecting and interlocking by having half slits (not shown) cut into each divider which are mutually engaged. This further division provides cassette 20 with twice as many compartments as cassette 10. All of the edges of horizontal divider 21 closely abut the adjacent inner surface portions of adjoining closure members, respectively, to prevent movement of bands identified for one compartment to an adjacent compartment during the sterilization process.

The cassette is manufactured in dimensions to allow it to be easily used with commonly available sterilization methods, such as placed in an autoclave, a dental ultrasonic sterilizing unit, or cold sterile containers. The cassette is further sized to allow use in those devices while allowing room for the sterilization of other dental instruments.

The cassette is further manufactured so that multiple cassettes can be placed together in a single case thereby reducing the storage room necessary for the cassettes.

While the invention has been described with reference to the preferred embodiments thereof, those skilled in the art will understand that variations in design, detail, size, shape and choice of materials for manufacture may be made and still fall within the spirit and scope of the present invention, which is intended to be limited only by the claims appended hereto.

I claim:

1. A method of organizing a plurality of orthodontic bands comprising the steps of:
   (a) providing a sterilization cassette of generally rectangular configuration having vertical sidewalls, vertical endwalls, a base and an opening on at least one side,
   (b) forming a plurality of discrete interior compartments in the sterilization cassette by dividing the interior of the cassette with a first set of generally parallel, dividing wall members supported within the cassette interior with each of the compartments being accessible through the open side of said sterilization cassette,
   (c) associating multiple indicia with each compartment identifying each compartment with respect to a jaw, a quadrant and a tooth of a patient's mouth;
   (d) closing the opening with a lid; and
   (e) preventing passage of an orthodontic band identified for one compartment to an adjacent compartment.

2. The method of claim 1 wherein the preventing passage step further comprises the step of:
   forming portions of each dividing wall member in closely abutting relation to the inner surface of its associated base, wall and lid portions.

3. The method of claim 2 wherein the forming portions step further comprises the step of:
   forming each wall member with edges closely abutting its associated adjacent base, wall and lid portions and flattening the edges sufficiently to limit the space therebetween, and
   wherein the closing step further comprises the step of closing the opening with a flat lid portion.

4. The method of claim 1 wherein the step of associating multiple indicia with each compartment further comprises the steps of:
   identifying each compartment with a first indicia indicating a jaw of a patient's mouth;
   identifying each compartment with a second indicia indicating a quadrant of a patient's mouth; and
   identifying each compartment with a third indicia indicating a tooth of a patient's mouth.

5. The method of claim 1 further comprising the step of:
   further dividing the cassette interior with at least one of a second set of dividing wall members perpendicularly intersecting with each of the parallel dividing wall members of the first set.

6. The method of claim 5 further comprising the step of:
   forming portions of each dividing wall member in closely abutting relation to the inner surface of its associated base, wall and lid portions.

7. The method of claim 6 wherein the forming portions step further comprises the steps of:
   forming each wall member with edges closely abutting its associated adjacent base, wall and lid portions and flattening the edges sufficiently to limit the space therebetween, and
   wherein the closing step further comprises the step of closing the opening with a flat lid portion.

8. The method of claim 1 further comprising the steps of:
   trial fitting at least one of a plurality of orthodontic bands to a patient's mouth, and
   sorting an orthodontic band into its identified one of the plurality of discrete interior compartments of the sterilization cassette.

9. The method of claim 8 wherein the trial fitting step further comprises the steps of:
   selecting at least one of a plurality of orthodontic bands and fitting the orthodontic band to the patient's tooth; and
   removing any of the plurality of orthodontic bands which are not appropriately fitted to the patient's tooth; and
   wherein the sorting step further comprises the step of:

placing any removed orthodontic band into its identified one of said plurality of discrete interior compartments of said sterilization cassette.

10. The method of claim 1 further comprising the step of:

placing an orthodontic band into its identified one of said plurality of discrete interior compartments of said sterilization cassette.

11. The method of claim 10 further comprising the step of:

sterilizing the sterilization cassette by passing sterilization fluid to each compartment through a plurality of holes in the cassette;

whereby orthodontic bands placed into each of said plurality of discrete interior compartments are sterilized while being retained within one of said plurality of discrete interior compartments and prevented from intermixing with orthodontic bands in another of said plurality of discrete interior compartments.

12. The method of claim 11 further comprising the step of:

inventorying the sterilized bands.

13. The method of claim 1 further comprising the step of:

forming the container and dividers of metal.

14. The method of manufacturing a sterilization cassette comprising the steps of:

(a) providing a sterilization cassette of generally rectangular configuration having vertical sidewalls, vertical endwalls, a base and an opening on at least one side, (b) forming a plurality of discrete interior compartments in the sterilization cassette by dividing the interior of the cassette with a first set of generally parallel, dividing wall members supported within the cassette interior with each of the compartments being accessibly through the open side of said sterilization cassette, (c) associating multiple indicia with each compartment identifying each compartment with respect to a jaw, a quadrant and a tooth of a patient's mouth;

(d) closing the opening with a lid; and (e) preventing passage of an orthodontic band identified for one compartment to an adjacent compartment.

* * * * *